US006861939B1

United States Patent
Bischof et al.

(10) Patent No.: US 6,861,939 B1
(45) Date of Patent: Mar. 1, 2005

(54) ARRANGEMENT OF A HEATING LAYER FOR A HIGH-TEMPERATURE GAS SENSOR

(75) Inventors: Michael Bischof, Kirchheim-Teck (DE); Burkhard Kessler, Laichingen (DE); Ralf Moos, Friedrichshafen (DE); Ralf Mueller, Aulendorf (DE); Willi Mueller, Salem (DE); Carsten Plog, Markdorf (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/890,613

(22) PCT Filed: Nov. 25, 2000

(86) PCT No.: PCT/EP00/11754

§ 371 (c)(1),
(2), (4) Date: Jul. 31, 2001

(87) PCT Pub. No.: WO01/40783

PCT Pub. Date: Jun. 7, 2001

(30) Foreign Application Priority Data

Dec. 2, 1999 (DE) .......................................... 199 57 991

(51) Int. Cl.[7] .............................................. H01C 7/10
(52) U.S. Cl. ............................. 338/23; 338/25; 338/28; 338/34; 219/482
(58) Field of Search ................................ 219/206, 205, 219/207, 482; 338/23, 24, 25, 28, 30, 34

(56) References Cited

U.S. PATENT DOCUMENTS

| | | | | |
|---|---|---|---|---|
| 4,286,377 A | * | 9/1981 | Hurko et al. .................. 29/612 |
| 4,345,465 A | * | 8/1982 | Gruner et al. ................. 338/28 |
| 4,375,056 A | * | 2/1983 | Baxter et al. .................. 338/25 |
| 4,464,646 A | * | 8/1984 | Burger et al. .................. 338/25 |
| 4,654,624 A | * | 3/1987 | Hagan et al. .................. 338/34 |
| 4,719,441 A | * | 1/1988 | Horn ........................... 338/20 |
| 4,776,943 A | * | 10/1988 | Kitahara ...................... 204/427 |
| 4,825,693 A | * | 5/1989 | Bohrer et al. ............. 73/204.25 |
| 4,861,456 A | * | 8/1989 | Mase et al. .................. 204/425 |
| 4,883,947 A | * | 11/1989 | Murase et al. ............... 219/553 |
| 5,017,340 A | * | 5/1991 | Pribat et al. ................. 210/543 |
| 5,169,512 A | * | 12/1992 | Wiedenmann et al. ...... 204/426 |
| 5,197,804 A | * | 3/1993 | Tani et al. ................... 374/185 |

(List continued on next page.)

FOREIGN PATENT DOCUMENTS

| | | |
|---|---|---|
| DE | 4324659 | 4/1995 |
| DE | 19523301 | 1/1997 |
| DE | 19848578 | 5/1999 |
| DE | 19830709 | 2/2000 |
| EP | 0477394 | 4/1992 |
| EP | 0720018 | 7/1996 |

OTHER PUBLICATIONS

Kurt Ingrisch et al.; "Chemical Sensors for CO/NO$_x$—Detection in Automotive Climate Control Systems"; SAE Technical Paper Series, No. 960692, International Congress & Exposition, Detroit, Michigan, Feb. 26–29, 1996, pp. 57–65.

K. Ingrisch, "Halbleiter Gassensoren"; K8/STZ2–Ingrisch; Robert Bosch GmbH, Oct. 27, 1997, TAE Essingen, Germany.

*Primary Examiner*—Karl D. Easthom
(74) *Attorney, Agent, or Firm*—W. F. Fasse; W. G. Fasse

(57) ABSTRACT

The operating temperature of a gas sensor capable of sensing a gas or a gas composition at a high temperature, for example 1000° C. is maintained constant over the entire volume of a gas sensor layer or function layer (4) secured to a sensor carrier section of the gas sensor by supplying heat to the gas sensor layer (4) in such a way that varying heat dissipations in the sensor carrier section are compensated. For this purpose, an electrical heater for heating the gas sensor layer (4) has individual heater sections with different heating resistance values which depend on a spacing between any individual heater section and the tip of the sensor carrier section.

13 Claims, 5 Drawing Sheets

U.S. PATENT DOCUMENTS

| | | | |
|---|---|---|---|
| 5,264,681 A | * 11/1993 | Nozaki et al. | 219/544 |
| 5,430,428 A | * 7/1995 | Gerblinger et al. | 338/25 |
| 5,605,612 A | * 2/1997 | Park et al. | 204/429 |
| 5,656,987 A | * 8/1997 | Kubota et al. | 338/7 |
| 5,726,624 A | * 3/1998 | Caffee et al. | 338/28 |
| 5,735,606 A | * 4/1998 | Tani et al. | 374/185 |
| 5,777,207 A | * 7/1998 | Yun et al. | 73/31.05 |
| 5,823,680 A | * 10/1998 | Kato et al. | 374/185 |
| 5,895,591 A | * 4/1999 | Kojima et al. | 219/209 |
| 6,437,981 B1 | * 8/2002 | Newton et al. | 338/2 |

* cited by examiner

ARRANGEMENT OF A HEATING LAYER FOR A HIGH-TEMPERATURE GAS SENSOR

FIELD OF THE INVENTION

The invention relates to an arrangement of a heating layer for a high-temperature gas sensor, especially for sensing a gas or gas mixture at high temperatures.

BACKGROUND INFORMATION

Sensors that are used in the exhaust gas of a combustion engine must not only be high-temperature stable, but rather they must typically also be regulated to maintain a determined operating temperature, because both the temperature of the exhaust gas as well as the exhaust gas throughput are dependent on the operating state of the engine and vary strongly. Such sensors are operated at several hundred degrees Celsius. A typical example is the λ-sonde which can be operated at temperatures up to 1000° C.

Other types of planar exhaust gas sensors, which are presently being produced by various manufacturers, consist of a structure as is shown in FIGS. 1a, 1b and 1c in various perspectives. In this context, FIG. 1a shows the top side of the sensor as a plan view, FIG. 1b shows the sensor in a side view on the section location marked with a dashed line, and FIG. 1c shows the bottom side of the sensor in a plan view. For orientation, a coordinate system with an x-, y and z-axis is drawn in. The Figures show an elongated rectangular carrier 1, also called a transducer, which generally consists of an electrically insulating substrate. A heating layer 8 is applied to the underside 5 as shown in FIGS. 1b and 1c. This heating layer 9 comprises a heating conductor path 6 and a supply line part 2. The heating conductor path 6 is located on the sensor bottom side under the functional layer 4, which is arranged on the sensor top side 7. The functional layer 4 determines the special characteristics of the sensor, such as, the selectivity for a certain gas or the like. Then, an electrode structure 3 adapted to the special requirements of a gas sensor is applied on the sensor top side 7 under the functional layer 4. A temperature that is constant over the location must prevail on the sensor tip 10 on the sensor top side 7, in the area in which the functional layer 4 is applied. This constant temperature is achieved with the aid of the heating layer 8 and a temperature sensor or feeler, which is not shown in this illustration but is located on the sensor bottom side. Thereby the functional layer 4 is regulated to a determined temperature, the so-called operating temperature.

A further function of the elongated appearing carrier is to ensure that the temperature on the side facing away from the sensor tip 10, the so-called sensor connection side 9, is so low that synthetic plastic insulated cables can be applied as measuring lines or as power supply lines on the end of the supply line part 2 of the heating layer 8.

For the functioning of the sensor, it is of decisive significance, how constant the temperature profile is on and over the functional layer 4, and how exactly the operating temperature can be regulated.

In the application example, the heating conductor path 6 is arranged as a heating meander. The uniform zig-zag shaped meander band runs parallel to the y-axis. The constant height A of the meander here corresponds to the length L of the functional layer 4 lying thereover. The width b of the heating conductor path 6 is constant. The two ends of the heating conductor path 6 are connected with the supply line part 2 of the heating layer 8. The supply line part 2 of the heating layer 8 is guided to the sensor connection side 9.

In the EP 0,720,018 A1, a heating layer for an exhaust gas sensor is disclosed, in which the heating conductor path 6 is arranged in a serpentine shaped manner. The spacing distance of the serpentines among each other is always the same. This form similarly corresponds to a uniformly modulating meander band that runs parallel to the y-axis of the sensor.

In the U.S. Pat. No. 5,430,428, DE 43 24 659 C1 and DE 198 30 709, similarly, forms for the extending path or progression of the heating conductor path in an exhaust gas sensor are disclosed. In this context, the heating conductor path is arranged in a meandering shape. However, the uniformly modulating meander band is arranged rectangularly and also runs parallel to the y-axis of the sensor.

In all of these publications, the heating conductor path has the form of a uniformly modulating meander band. The height A of the meander band is constant during the entire extension or path progression.

A similar construction of various gas sensors is also described in the script "Industrial Gas Sensor Arrangements", especially in part 4 by K. Ingrisch: "Semi-conductor Gas Sensors" of the Instruction Course 22904/41.551 at the TAE Esslingen; G. Wiegleb (production); Esslingen 1997 and in the SAE-Paper 960692 by K. Ingrisch et al.: "Chemical Sensors for $CO/NO_x$-Detection in Automotive Climate Control Systems".

Arrangements of the heating layer 8 in high-temperature gas sensors are also known in which the heating conductor path 6 forms a meander band, which, beginning at the supply line part 2, first extends uniformly modulating on the one side parallel to the x-axis, and then extends in a straight line along the sensor tip parallel to the y-axis, and then again extends on the other side uniformly modulating parallel to the x-axis back to the supply line part 2. The width b of the heating conductor path 6 is not varied. The length L of the region in which the heating conductor path 6 is arranged, corresponds to the length L of the functional layer 4 lying thereover. Such a construction is disclosed, for example, in the DE 198 48 578 A1.

It is disadvantageous in all of the previously described arrangements, that a temperature gradient arises along the lengthwise axis x of the sensor, necessitated by the good thermal conductivity of the typically utilized $Al_2O_3$ substrate. This temperature gradient is subject to very large fluctuations. Thus, for a rated temperature of, for example, 600° C., this temperature gradient typically amounts to approximately BOC over the length L of the functional layer 4, as it is shown in FIG. 2b. In FIG. 2b, the temperature at various points on the sensor top side is illustrated.

In order to make the temperature distribution on the sensor top side more homogeneous, it is suggested in the EP 0,477,394 to build up or construct the heating conductor paths on the sensor tip in the form of a ladder, whereby the ladder pattern contains a plurality of parallel circuit-connected individual conductors, which can be arranged so that a homogeneous temperature distribution can be adjustably set over the length. In this context, both the width or the cross-section of the various heating conductor paths as well as the spacing between two heating conductor paths, which represent the spokes of the ladder formation, can vary.

It is disadvantageous in this publication, however, that due to the parallel circuit connection, the resistance of the heating conductor paths is reduced so far or so low that it is no longer possible to establish a resistance in the range of several ohms for the same specific resistance of the heating conductor path resistance (generally platinum), because otherwise the layer thickness of the structure would have to become so thin that it could no longer be produced by thick layer or thick film technology.

In the DE 195 23 301, a heating arrangement for a high-temperature metal oxide sensor is disclosed, in which a substrate is provided, on which, in addition to the two supply line parts of the heating layer, two measuring conductor paths are arranged, which are connected to the heating conductor path, and wherein one or more connection lines are secured to a location on the supply line part of the heating layer that is as far away as possible from the heating conductor path. This arrangement in four wire technology is illustrated as a substitute circuit diagram in FIG. 3. That means, that in addition to the wide supply line parts of the heating layer, two additional measuring lines are introduced, on which the voltage drop over the heating resistance of the heating conductor path is tapped or taken-off. In this arrangement, it is irrelevant how large the resistances $R_{21}$ and $R_{22}$ of the supply line parts of the heating layer are, because the voltage $U_H$ is directly taken-off or tapped on the heating resistance $R_H$ of the heating conductor path. Since the voltage $U_M$ is measured in a zero-current condition, no voltage will drop across the two tapping resistors $R_{A1}$ and $R_{A2}$. The resistance can be determined as $R_H=U_H/I_0$ from the measured current $I_0$ and the voltage $U_M$. A simplified embodiment thereof is also known as state of the art, namely the so-called three-wire technology. If one assumes the two resistances of the supply line parts of the heating layer to be equal, then one can omit one of the two voltage taps. Then, one must only still measure the total voltage $U_0$ and then obtains: $R_H=(2xU'_M-U_0)/I_0$. One measuring conductor and one connection contact are saved through this three-wire technology.

It is disadvantageous in this publication, however, that the temperature profile of the sensor is not constant over the length L in the x-direction, and thus the heating resistance of the heating conductor path is only to be regarded as an average value over the entire range L. Therefore, a regulation can similarly only be achieved very inexactly therewith. This is especially of disadvantage, if the temperature of the sensor housing changes strongly, as is the case, for example, in the exhaust gas of an automobile, because then the temperature gradient similarly strongly varies over the sensor chip, and thus RH can be allocated to no temperature of the functional layer.

SUMMARY OF THE INVENTION

It is the object of the invention to arrange the heating conductor path(s) so that substantially the same temperature prevails at each location of the functional layer of the sensor. It is a further object of the invention to provide a fundamental basis with which an exact temperature determination, and connected therewith, an exact temperature regulation or closed loop control of the temperature of the functional surface, is made possible.

This object is achieved according to the invention by a gas sensor for sensing a gas or gas composition at high temperatures, said gas sensor comprising a; substrate having a sensor carrier section with a tip and a conductor carrier section connected to said sensor carrier section opposite said tip, a gas sensor function layer supported by said sensor carrier section of said substrate next to said tip, an electrical heater supported by said sensor carrier section in a position for heating said gas sensor function layer, electrical conductors supported on said conductor carrier section of said substrate and electrically connected to said electrical heater said electrical ate heater sections having different heating resistance values which depend on a spacing between any particular heater section and said tin of said sensor carrier section for generating a constant operating temperature throughout said gas sensor function layer by compensating varying heat dissipations by said substrate in said sensor carrier section. In this context, the meander-shaped heating conductor path comprises different partial heating resistances in different partial sections with reference to the x-axis. The height or magnitude of the partial heating resistance is dependent on the spacing distance relative to the sensor tip.

According to further advantageous embodiments of the invention the partial heating resistance decreases or diminishes in a direction toward the sensor tip. This is achieved in that the path length of the heating conductor path and therewith of the meander band varies from partial section to partial section. In this context, the path length of the heating conductor band is given if one would pull apart the meander band like a thread that is looped or tangled in itself. The width of the heating conductor path can also vary in various partial sections, alone or together with the path length. Moreover, in addition to the supply lines of the heating layer, measuring supply lines are also applied, with which the exact temperature can be obtained, so that an exact temperature regulation is made possible. An exact temperature regulation is provided by a closed loon control. In a further advantageous embodiment, the heating resistance to be measured can be adjustingly set, so that plural sensors comprise an identical resistance/temperature characteristic curve.

The advantages achieved with the invention consist in that the sensor, and especially the functional surface of a high-temperature gas sensor, can be adjustingly set to an exact temperature, which then prevails at each location on the functional surface.

The heated surface then comprises a minimal temperature gradient which means that the temperatures of the function layer is substantially constant. The temperature measurement provides more exact results and the entire high-temperature gas sensor works with a higher accuracy. Also, thereby the sensors may be normed or normalized among one another, so that the same temperature can be allocated for the same measured heating resistance of various sensors.

BRIEF DESCRIPTION OF THE DRAWINGS

The invention shall be described in the following in greater detail in connection with example embodiments and the Figures.

FIG. 2b shows the temperature distribution for a high-temperature gas sensor with the heating layer shown in FIG. 2a.

FIG. 4b shows the diagram of the temperature distribution for a high-temperature gas sensor with a heating conductor path shown in FIG. 4a.

FIG. 5b shows the diagram of the temperature distribution for a high-temperature gas sensor with a heating conductor path shown in FIG. 5a.

DETAILED DESCRIPTION OF PREFERRED EXAMPLE EMBODIMENTS AND OF THE BEST MODE OF THE INVENTION

Figure 4A:
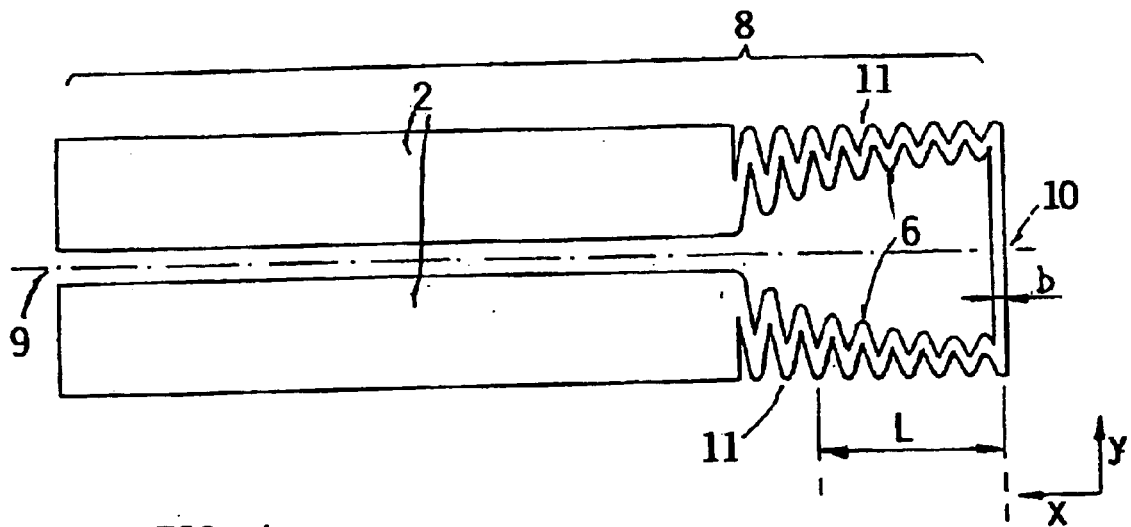
FIG. 4a shows the first heating layer with a meander-shaped heating conductor path and different partial resistances.

FIG. 4a shows a heating layer arrangement with a heating conductor path 6, of which the extending path or progression forms a meander-band, which, beginning on the electric power supply line part 2 also referred to herein as electric power supply conductors 2, first extends modulatingly on the one side parallel to the x-axis, and then extends in a straight line along the sensor tip parallel to the y-axis, and then again extends on the other side modulatingly parallel to the x-axis back to the electric power supply line part 2. In this context, the heating layer 8 was produced with a platinum thick film paste, which was applied by a screen printing technique onto an aluminum oxide substrate and thereafter was fired. For achieving a homogeneous temperature profile, the partial heating resistance in the x-direction was varied. The partial heating resistance is proportional to the quotient of the path length 1 and the width of the heating conductor path b relative to a path distance in the x-direction.

In order to adapt the heating resistance to the desired temperature profile, that is to say the same or constant temperatures over the entire functional layer 4 in the example embodiment, the path length 1 of the heating pr/conductor path 6 is shortened from partial section to partial section, in that the height or amplitudes of the meander-band 11 is steadily reduced from section to section. It would also be exactly as effective to reduce the modulation rate, namely the frequency of the direction change of the meander-band 11, with reference to a path distance in the x-direction.

The relationship between the path length 1 of the heating conductor path 6 and the proportion of the path distance covered or traversed in the x-direction is important. Thereby, the partial heating resistance per unit length in the x-direction can be varied. Thus, different energy quantities can be supplied to the functional layer at different locations.

In this application example, a constant heating conductor path width b of b=300 μm was selected. It is also evident in this illustration, that the area or region in which the heating conductor path 6 is applied, is substantially longer than the length L of the functional layer 4 which lies over the path 6. The heating conductor path 6 has a meander-shape, and is arranged between the outer or tip end of the functional layer 4 and the supply line part 2. The path 6 is positioned to heat the gas sensor function layer 4. More specifically, the heater path 6 serves to compensate and to provide counter heating for the heat flow and dissipation to the sensor connection side 9. In order to achieve this, compensation most of the heat energy, that is to say the greatest proportion along the entire length of the heating conductor path 6 is required. The high resistance value per unit length in the x-direction is achieved by the long winding shape of the heating conductor path 6. Which resistance value is required at which location can either be calculated or determined by experiments.

Figure 1A:
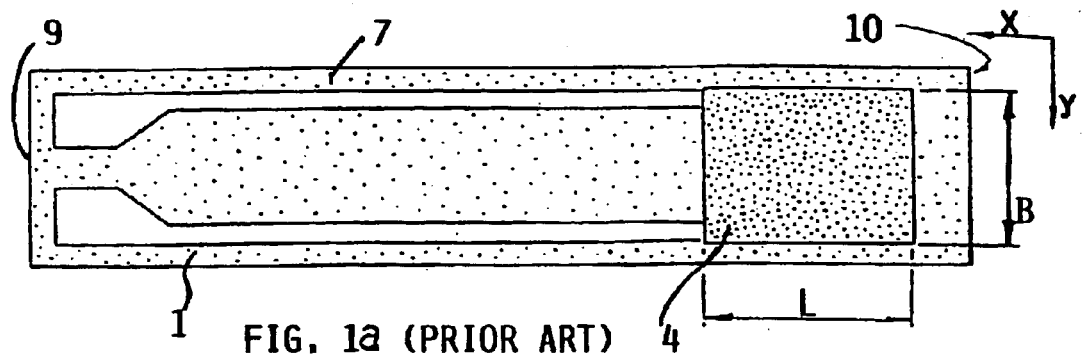
FIG. 1a shows the top side of a high-temperature gas sensor according to the prior art.
Figure 1B:
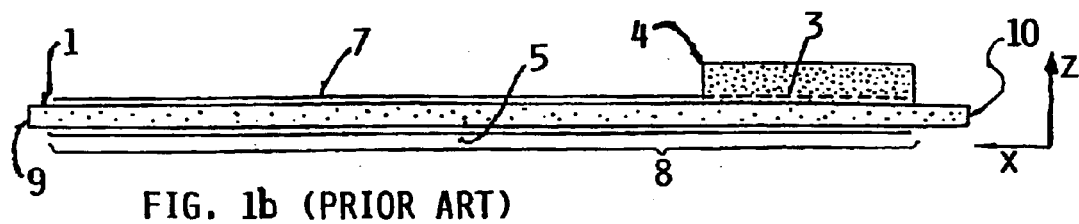
FIG. 1b shows the side view of a high-temperature gas sensor according to the prior art.
Figure 1C:
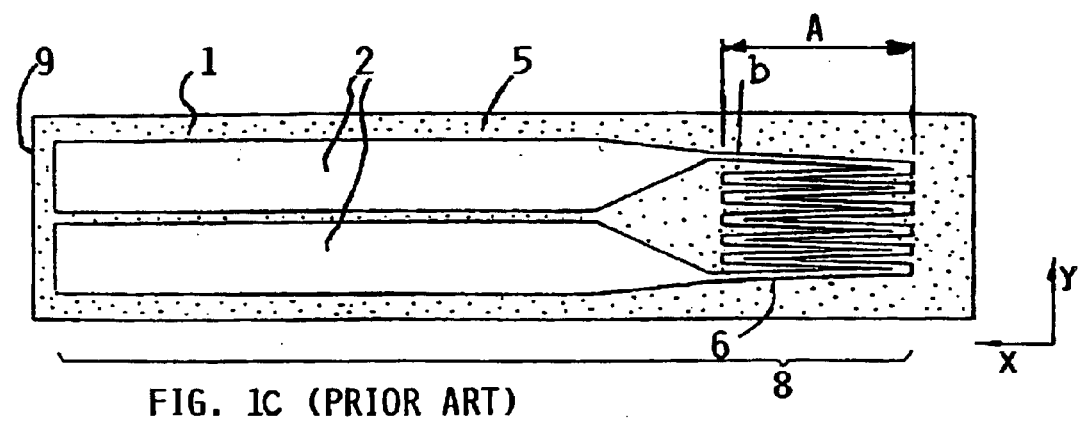
FIG. 1c shows the bottom side of a high-temperature gas sensor with a first heating layer according to the prior art.
Figure 2A:
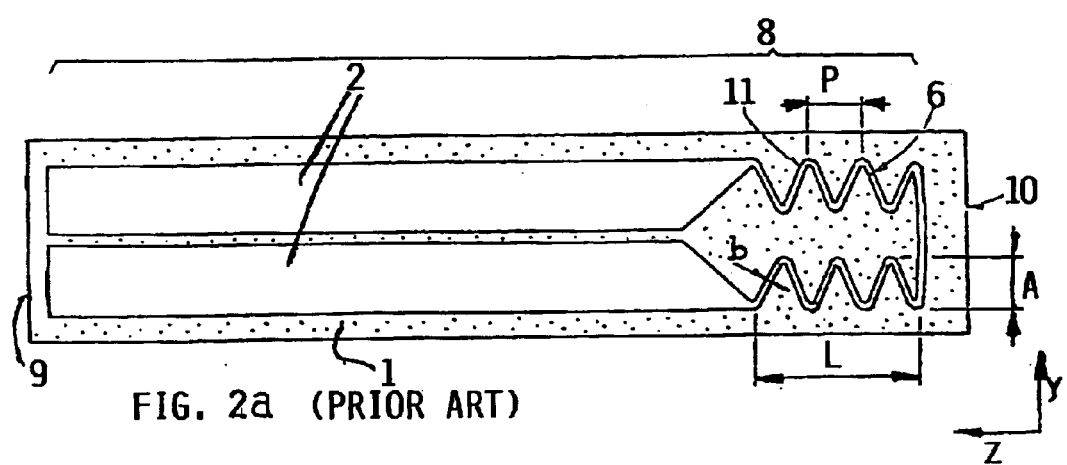
FIG. 2a shows the bottom side of a high-temperature gas sensor with a second heating layer according to the prior art.
Figure 2B:
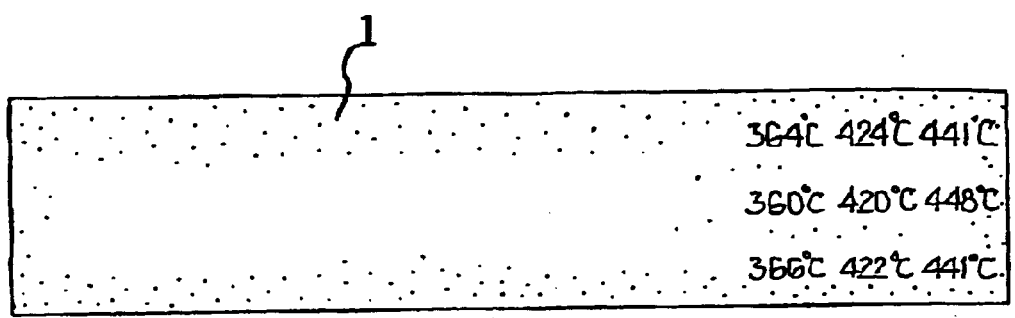
Figure 4B:
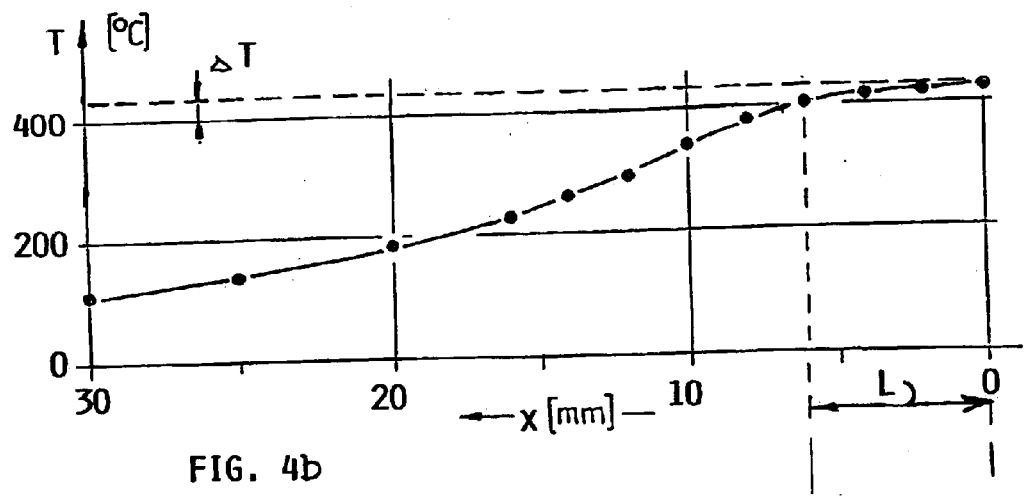

FIG. 4b shows the temperature distribution curve along the x-axis for a high-temperature gas sensor with a heating conductor path shown in FIG. 4a. In this context, the temperature along the x-axis over the entire sensor is detected or obtained dependent on the spacing distance relative to the sensor tip. It can be seen that the temperature in the region of the length L of the am functional layer comprises only a very small temperature fluctuation ΔT in the x-direction. Compared to the temperature distribution shown in FIG. 2b, there is achieved a temperature fluctuation ΔT that is smaller by 60° C.

Figure 5A:
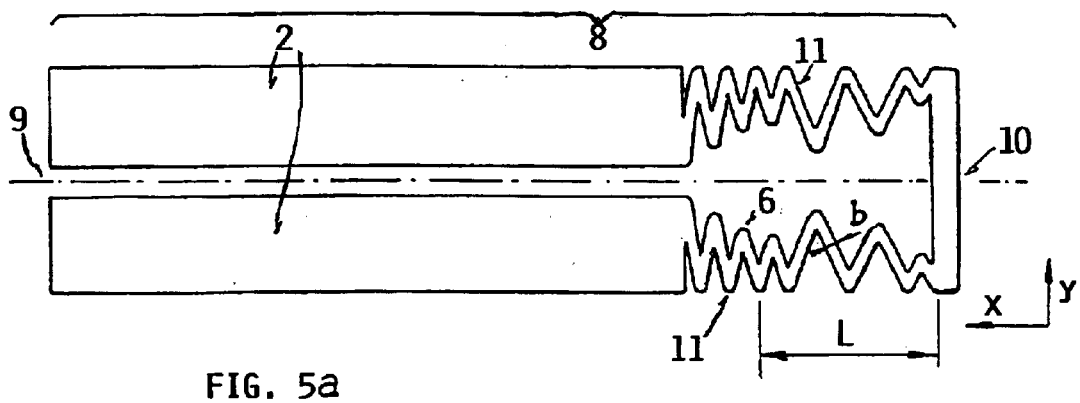
FIG. 5a shows the second heating layer with a meander-shaped heating conductor path and different partial resistances.

FIG. 5a shows a heating layer arrangement with a heating conductor path 6, of which the extending path or progression forms a meander-band, which, beginning on the supply line part 2, first extends modulatingly on the one side parallel to the x-axis, and then extends in a straight line along the sensor tip parallel to the y-axis, and then again extends on the other side modulatingly parallel to the x-axis back to the supply line part 2. In this context, the heating layer 8 was produced with a platinum thick film paste, which was applied by a screen printing technique onto an aluminum oxide substrate and thereafter was fired. For achieving a homogeneous temperature profile, the partial heating resistance in the x-direction was varied. The partial heating resistance is proportional to the quotient of the path length 1 and the width of the heating conductor path b relative to a path distance in the x-direction. In order to adapt the heating resistance to the desired temperature profile, that is to say the same temperatures over the entire functional layer, in the example embodiment, the path length 1 of the heating conductor path 6 is shortened from partial section to partial section, in that both the height A of the meander-band 11 as well as the modulation rate, i.e. the frequency of the direction change of the meander-band 11 in the x-direction, and the width b of the heating conductor path are varied, so that the partial heating resistance decreases or diminishes toward the sensor tip.

The relationship between the path length of the heating conductor path 6 and the proportion of the path distance covered or traversed in the x-direction is important. Thereby, the partial heating resistance per unit length in the x-direction can be varied. Thus, different energy quantities can be supplied to the functional layer at different locations. Also the width b of the heating conductor path is of significance. The shorter the path length of the heating conductor path and the larger its width in a partial section, the smaller is the partial heating resistance of the heating conductor path region, and thus, the smaller is the heating in this region.

In this application example, the heating conductor path comprises varying widths b. In the two sections that extend along to the x-axis, the heating conductor path width amounts to b=300 µm. On the straight section, which extends parallel to the y-axis on the sensor tip, the value increases to b=600 µm. Also here, the heating conductor path arranged in a meander-shape, which is arranged between the end of the functional layer 4 lying thereover and the supply line part 2, again serves to compensate and to provide counter-heating for the heat flow to the sensor connection side 9. In order to achieve this, the most heating power, that is to say the greatest proportion on the path length of the heating conductor path is needed. In this application example, it is not absolutely necessary, that the two meander-shaped partial parts are axially symmetrical. The required so resistance values may also be achieved by a variation of other parameters. They also need not extend exactly parallel. This is, however, especially advantageous, if the temperature gradient in the y-direction shall be very small, because then the curve progression does not need to be separately determined once again.

Figure 5B:
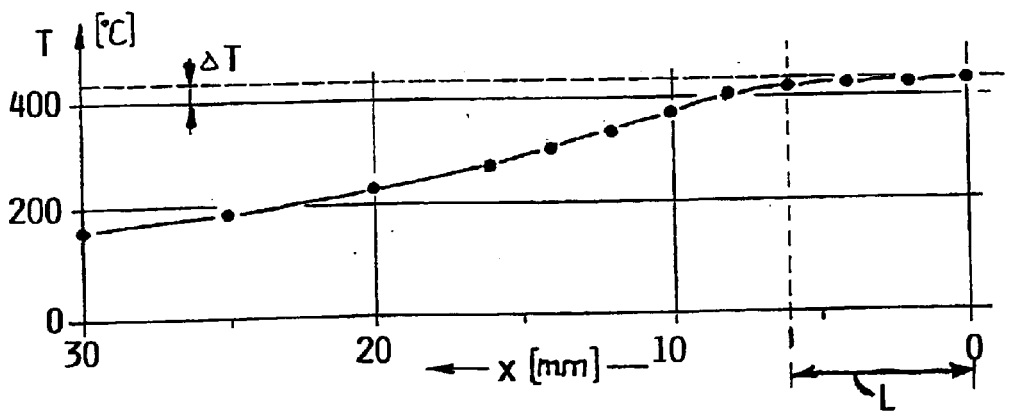

FIG. 5b shows a diagram of the temperature distribution for a high-temperature gas sensor with a heating conductor path shown in FIG. 5a. In this context, the temperature along the x-axis over the entire sensor is determined or obtained dependent on the spacing distance relative to the sensor tip. It can be seen that the temperature fluctuation ΔT in the region length L of the functional layer has been further reduced in comparison to FIG. 4b.

From the previously described example embodiments it becomes clear, that the characteristic values, the width b of the heating conductor path and the path length 1 of the heating conductor path, are varied in order to obtain a homogeneous temperature distribution. These characteristic values can be varied both individually as well as in all possible combinations, along the heating conductor path progression. Thereby, the path length can be varied both by the height A of a meander-band 11 as well as by the modulation rate, i.e. the frequency of the direction change in the x-direction of the meander-band 11.

In the further Figures, embodiments are presented, which make it possible, due to the homogeneous temperature distribution, to determine the temperature on the sensor surface exactly in the region in which the functional layer is located.

Figure 6:
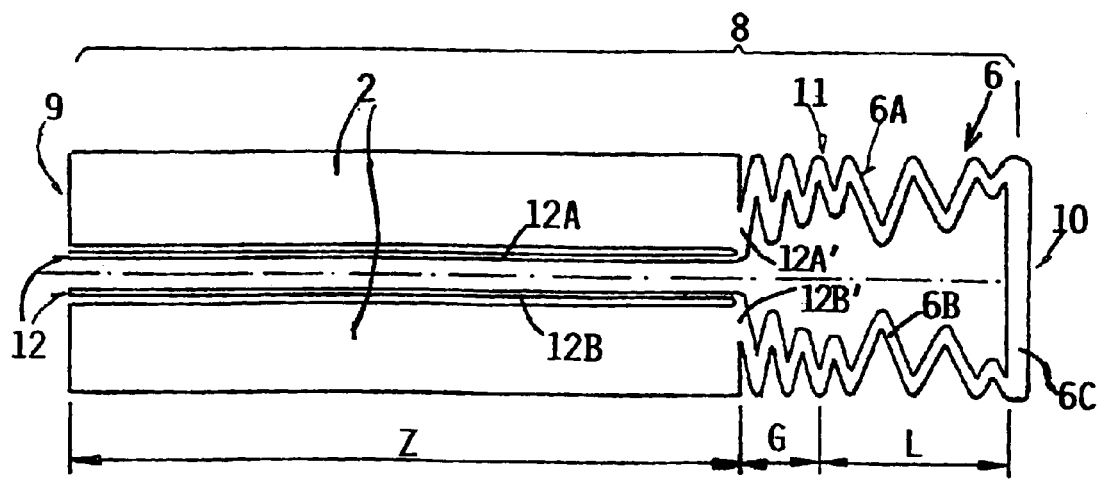
FIG. 6 shows the heating layer with a first additional arrangement for measuring lines for the temperature determination.

FIG. 6 shows a heating layer with a first additional arrangement of at least one temperature sensing conductor path 12 for sensing the temperature of the sensor section formed by the regions G+L. The conductor path 12 has, for example, two sensor conductors 12A and 123 connected to respective contact points 12A' and 12B' forming serve as voltage taps. The sensor conductors 12A and 12B are parallel to the broad power supply line parts 2 which supply electrical power to the heating conductor path 6 from the sensor connection side 9. The heating conductor path 6 is also referred to simply 4 as heater 6. The sensor connection side 9 is also referred to as a conductor carrier section 9. By this arrangement, the supply line resistance, that is to say the voltage drop over the power supply line parts 2 or electric power supply conductors 2, is compensated over the path distance Z, but the portion of the resistance or respective voltage drop in the region G, which serves for the counter-heating or heat dissipation compensation, is measured, for producing a heat supply control signal. Since, however, the largest temperature gradient lies in the region G, as described in the preceding example embodiments, and because the greatest portion of the total path length of the heater 6 is provided in the region G, the resistance arises as a combination of the resistance portions of the heating conductor path of the partial paths distances or length in the regions G and L. Only the resistance portion at L is measured at a temperature that is constant in the region of L. If the temperature gradient at G is the same for all conditions, then the measuring result can be exactly evaluated.

FIG. 6 also shows that the heater 6 has two meandering heater paths 6A and 6B connected in series with each other by an intermediate heater portion 6C. The series connection of 6A, 6B and 6C is connected to the electric power supply conductors 2.

With strongly fluctuating surrounding environmental temperatures, which is the case, for example, in an application in the exhaust gas of an automobile, the temperature gradient in the region of G will vary. Then it makes sense to arrange the measuring lines as it is described in FIG. 7.

Figure 7:
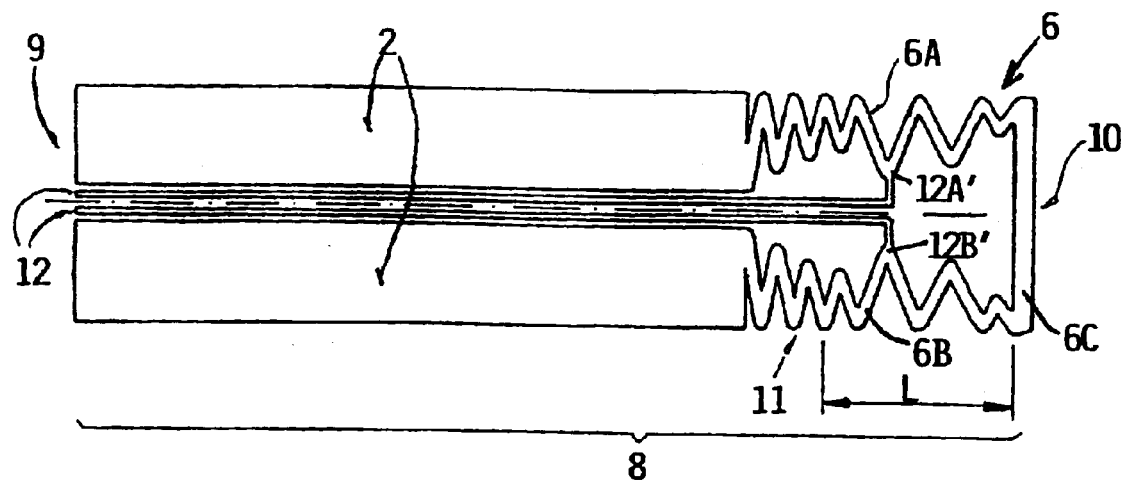
FIG. 7 shows the heating layer with a second additional arrangement for measuring lines for the temperature determination.
Figure 8:
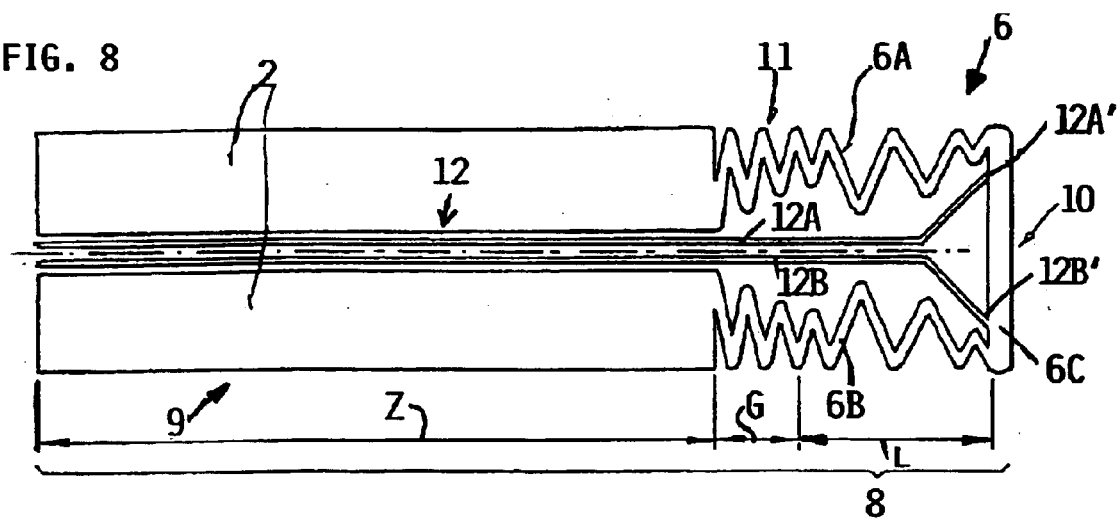
FIG. 8 shows the heating layer with a third additional arrangement for measuring lines for the temperature determination.

In FIGS. 7 and 8, two measuring conductor paths 12 for temperature determination are similarly applied. Here, however, the voltage is tapped in a region at which a constant temperature prevails. That is to say, the measuring conductor paths 12 can be applied everywhere on the heating conductor path 6, somewhere in the region of L at a desired location, in a symmetrical manner. Here it is similarly possible, through the measurement of the resistance, to measure and therewith also regulate the temperature.

Figure 9:
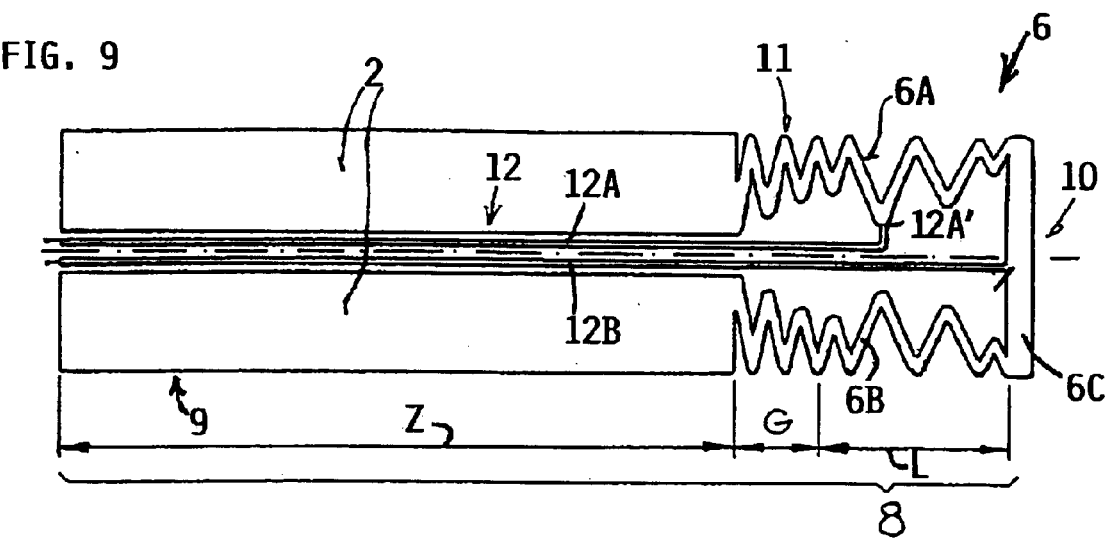
FIG. 9 shows the heating layer with a fourth additional arrangement for measuring lines for the temperature determination.

In FIG. 9, two asymmetrical measuring conductor paths 12 for the temperature determination are applied. Here the voltage is also tapped in a region at which a constant temperature prevails. That is to say, they can be applied everywhere on the heating conductor path 6, somewhere in the region of L, at a desired location, in an asymmetrical manner. Here it is similarly possible, through the measurement of the resistance, to measure and therewith also regulate the temperature.

Figure 10:
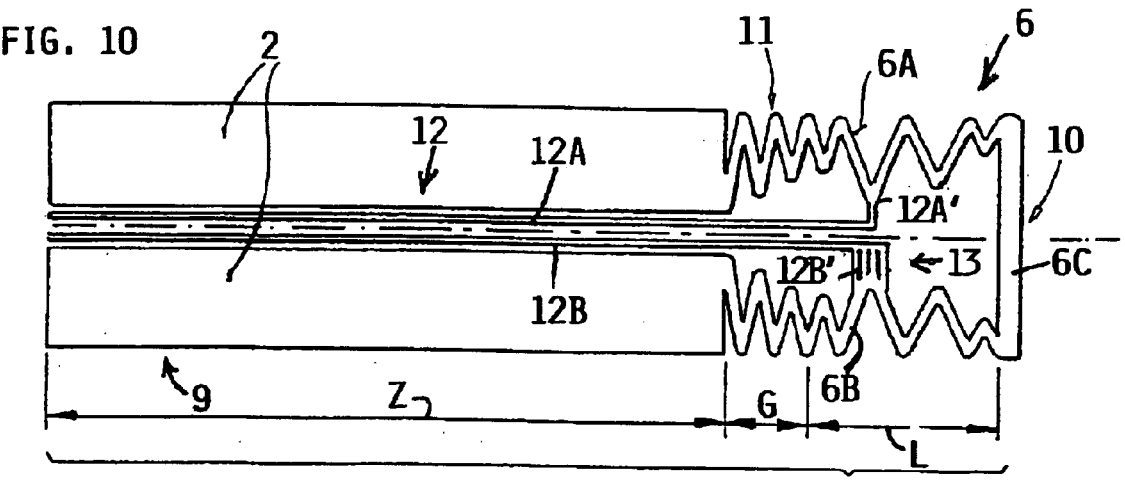
FIG. 10 shows the heating layer with a fifth additional arrangement for measuring lines for the temperature determination.

FIG. 10 shows a heating layer with a variable arrangement for measuring conductor paths 12 for the temperature determination. In this, context, the voltage taps are applied at various different locations 13 within the path distance L. In the further production process, the individual voltage taps can be severed or trimmed in such a manner by means of a laser method so that only one connection remains, which offers exactly the desired resistance value. In this manner, fluctuations during the production, for example of the layer thickness or of the specific resistance of the heating conductor path material, can be compensated, in order to obtain thereby a constant relationship between measured resistance value and temperature for all sensors. In this context, also the total resistance of the heating conductor path 6 remains unchanged. Sensors fabricated in this manner will then all comprise a common resistance-temperature characteristic curve. Contrary to conventional structures, for which complicated trimming must be carried out on the sensor connection side through variation of the total resistance, here the trimming takes place by variation of the voltage tap on the high-temperature side.

FIGS. 5a and 6 to 10 show that the heater paths 6A and 6B which are connected in series by the intermediate heater section 6C, form each two groups of heater sections with meandering amplitudes that diminish toward the tip 10 of the sensor. More specifically, the amplitudes of the first group diminish toward the second group of amplitudes which start with a larger amplitude and then also diminish toward the tip.

Figure 3:
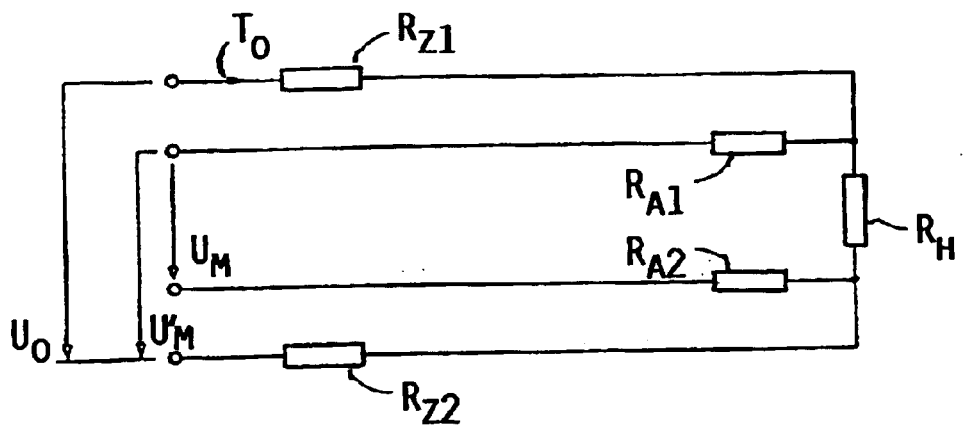
FIG. 3 shows the circuit for the temperature measurement on a high-temperature gas sensor according to the prior art.

It is evident for all applications, that the measuring conductor paths cannot only be fabricated as shown in the four-wire technique, but also analogously may be fabricated in the three-wire technique, as already described in FIG. 3.

Although the invention has been described with reference to specific example embodiments, it will be appreciated that it is intended to cover all modifications and equivalents within the scone of the appended claims. It should also be understood that the present disclosure includes all possible combinations of any individual features recited in any of the appended claims.

What is claimed is:

1. A gas sensor for sensing a gas or gas composition at high temperatures, said gas sensor comprising a substrate (1) having a sensor carrier section with a tip (10) and a conductor carrier section (9) connected to said sensor carrier section opposite said tip (10), said sensor carrier section having zones with varying heat dissipations, a gas sensor function layer (4) supported by said sensor carrier section of said substrate (1) next to said tip (10), an electrical heater (6) supported by said sensor carrier section in a position for heating said gas sensor function layer (4), electric power supply conductors (2) supported on said conductor carrier section (9) of said substrate (1) and electrically connected to said electrical heater (6), said electrical heater (6) comprising heater sections having different heating resistance values which depend on a spacing between any particular heater section and said tip (10) of said sensor carrier section, said different heating resistance values generating varying amounts of heat for compensating said varying heat dissipations, said gas sensor further comprising at least one temperature sensing conductor path (12) electrically connected to said electrical heater (6) at least at one contact point, wherein said at least one contact point between said electrical heater (6) and said at least one temperature sensing conductor path (12) is positioned on said sensor carrier section for measuring an operating temperature of said sensor carrier section to provide a closed loop control signal for said electrical heater to maintain said operating temperature at a minimal temperature gradient throughout said gas sensor function layer, wherein said electrical heater (6) comprises two meandering heater paths (6A, 6B) and an intermediate non-meandering heater portion (6C) positioned next to said tip (10), said intermediate non-meandering heater portion (6C) electrically connecting said two meandering heater paths (6A, 6B) in series with each other, said meandering heater paths (6A, 6B) having amplitudes forming said heater sections, and wherein said amplitudes except a first largest amplitude of said meandering heater paths are diminishing in their size relative to and from said first largest amplitude toward said tip (10) depending on said spacing between any particular heater section formed by a respective amplitude and said tip (10).

2. The gas sensor of claim 1, wherein said two meandering heater paths (6A, 6B) of said electrical heater (6) comprise a heater path width (b) along said heater sections, said path width (b) varying depending on said spacing between any particular heater section and said tip (10).

3. The gas sensor of claim 1, wherein said gas sensor function layer (4) has a length (L) between said conductor carrier section and said tip (10) and wherein said at least one contact point is located along said length (L) of said gas sensor function layer (4) and below said gas sensor function layer (4).

4. The gas sensor of claim 1, comprising two temperature sensing conductor paths (12A, 12B) and at least two contact points (12A' and 12B') between said two temperature sensing conductor paths (12A, 12B) and said electrical heater (6) for selecting a different resistance value from at least two different resistance values of said electrical heater (6).

5. The gas sensor of claim 1, wherein said gas sensor function layer (4) is secured to one surface of said sensor carrier section of said substrate (1), and wherein said electrical heater (6) is attached to an opposite surface of said sensor carrier section of said substrate (1) in said position for heating said gas sensor function layer (4).

6. A gas sensor for sensing a gas or gas composition at high temperatures, said gas sensor comprising a substrate (1) having a sensor carrier section with a tip (10) and a conductor carrier section (9) connected to said sensor carrier section opposite said tip (10), said sensor carrier section having zones with varying heat dissipations, a gas sensor function layer (4) supported by said sensor carrier section of said substrate (1) next to said tip (10), an electrical heater (6) supported by said sensor carrier section in a position for heating said gas sensor function layer (4), electric power supply conductors (2) supported on said conductor carrier section (9) of said substrate (1) and electrically connected to said electrical heater (6), said electrical heater (6) comprising heater sections having different heating resistance values which depend on a spacing between any particular heater section and said tip (10) of said sensor carrier section, said different heating resistance values generating varying amounts of heat for compensating said varying heat dissipations, said gas sensor further comprising two temperature sensing conductor paths (12A, 12B) electrically connected to said electrical heater (6) at two respective contact points, positioned on said sensor carrier section for measuring an operating temperature of said sensor carrier section to provide a closed loop control signal for said electrical heater to maintain said operating temperature at a minimal temperature gradient throughout said gas sensor function layer, and wherein said electrical heater (6) comprises an intermediate non-meandering heater portion (6C) and at least two meandering heater paths (6A, 6B) electrically connected in series with each other by said intermediate non-meandering heater portion (6C) to form an electrical heater series connection, wherein said two respective temperature sensing conductor paths (12A, 12B) are connected to said electrical heater series connection at said two respective contact points, (12A', 12B'), and wherein said two contact points (12A', 12D') are spaced from each other along said electrical heater series connection at a predetermined spacing between said two contact points.

7. The gas sensor of claim 6, wherein said gas sensor function layer (4) is secured to one surface of said sensor carrier section of said substrate (1), and wherein said electrical heater (6) is attached to an opposite surface of said same sensor carrier section of said substrate (1) in said position for heating said gas 7 sensor function layer (4).

8. The gas sensor of claim 6, wherein said electrical heater (6) comprises a heater path having a path width (b) along said heater sections, said path width (b) varying depending on said spacing between any particular heater section and said tip (10).

9. The gas sensor of claim 6, wherein said gas sensor function layer (4) has a length (L) between said conductor carrier section and said tip (10) and wherein at least one contact point of said two contact points is located along said length (L) of said gas sensor function layer (4) and below said gas sensor function layer (4).

10. A gas sensor for sensing a gas or a gas composition at high temperatures, said gas sensor comprising a substrate (1) including a sensor carrier section with a tip (10) and a gas sensor function layer (4) supported by said sensor carrier section, an electrical heater (6) supported by said sensor carrier section, said electrical heater comprising at least one meandering heater a path including amplitudes forming heater sections, wherein a first heater section has the largest amplitude and each heater section has a different heating resistance value which depends on a spacing between said tip (10) and a respective heater section of said heater sections, and wherein a second and further amplitudes of said amplitudes forming said heater sections diminish toward said tip (10) relative to said largest amplitude of said first heater section for maintaining an operating temperature of said sensor carrier section at a minimal temperature gradient throughout said gas sensor function layer (4).

11. The gas sensor of claim 10, further a comprising at least one temperature sensing conductor path (12) electrically connected to said electrical heater (6) for measuring said operating temperature to provide a control signal for controlling said operating temperature.

12. The gas sensor of claim 10, wherein said gas sensor function layer (4) is secured to one surface of said sensor carrier section of said substrate (1), and wherein said electrical heater (6) is attached to an opposite surface of said sensor carrier section of said substrate (1) in said position for heating said gas sensor function layer (4).

13. A gas sensor for sensing a gas or a gas composition at high temperatures, said gas sensor comprising a substrate (1) including a sensor carrier section with a tip (10) and a gas sensor function layer (4) supported by said sensor carrier section, an electrical heater (6) supported by said sensor carrier section, said electrical heater comprising at least one meandering heater path including amplitudes forming heater sections, each heater section having a different heating resistance value which depends on a spacing between said tip (10) and a respective heater section of said heater sections, wherein said heater sections form at least two groups of heater sections, and wherein second and further amplitudes of said amplitudes forming each group of said heater sections diminish toward said tip (10) relative to a largest amplitude in each group of heater sections for maintaining an operating temperature of said sensor carrier section at a minimal temperature gradient throughout said gas sensor function layer (4).

\* \* \* \* \*

UNITED STATES PATENT AND TRADEMARK OFFICE
CERTIFICATE OF CORRECTION

PATENT NO. : 6,861,939 B1
DATED : March 1, 2005
INVENTOR(S) : Bischof et al.

It is certified that error appears in the above-identified patent and that said Letters Patent is hereby corrected as shown below:

<u>Title page,</u>
Item [56], References Cited, U.S. PATENT DOCUMENTS, replace "6,437,981 B1 8/2002 Newton et al" by -- 6,437,681 B1 8/2002 Wang et al. --;

<u>Column 2,</u>
Line 48, after "approximately", replace "BOC" by -- 80°C --;

<u>Column 3,</u>
Line 59, before "substrate", delete -- ; --;
Line 67, after "heater", insert -- , --;

<u>Column 4,</u>
Line 1, after "electrical", delete -- are --;
Line 1, after "heater", insert -- comprising heater --;
Line 3, after "said", replace "tin" by -- tip --;

<u>Column 5,</u>
Line 53, before "path", replace "pr/conductor" by -- conductor --;
Line 60, after "length", replace "1" by -- I --;

<u>Column 6,</u>
Line 10, after "this", delete -- , --;
Line 23, before "functional", delete -- am --;

<u>Column 7,</u>
Line 48, before "connected", replace "123" by -- 12B --;
Line 49, after "forming", delete -- serve as --;
Line 54, after "simply", delete -- 4 --;

<u>Column 8,</u>
Line 37, after "this", delete -- , --;

UNITED STATES PATENT AND TRADEMARK OFFICE
CERTIFICATE OF CORRECTION

PATENT NO.    : 6,861,939 B1
DATED         : March 1, 2005
INVENTOR(S)   : Bischof et al.

It is certified that error appears in the above-identified patent and that said Letters Patent is hereby corrected as shown below:

Column 10,
Line 48, after "gas", delete -- 7 --;
Line 66, after "heater", delete -- a --.

Signed and Sealed this

Twenty-eighth Day of June, 2005

JON W. DUDAS
*Director of the United States Patent and Trademark Office*